US008355512B2

(12) United States Patent
Pan et al.

(10) Patent No.: US 8,355,512 B2
(45) **Date of Patent: *Jan. 15, 2013**

(54) ACTIVE NOISE REDUCTION ADAPTIVE FILTER LEAKAGE ADJUSTING

(75) Inventors: Davis Y. Pan, Arlington, MA (US); Eduardo T. Salvador, Cambridge, MA (US)

(73) Assignee: Bose Corporation, Framingham, MA (US)

( * ) Notice: Subject to any disclaimer, the term of this patent is extended or adjusted under 35 U.S.C. 154(b) by 759 days.

This patent is subject to a terminal disclaimer.

(21) Appl. No.: 12/254,037

(22) Filed: Oct. 20, 2008

(65) Prior Publication Data

US 2010/0098263 A1 Apr. 22, 2010

(51) Int. Cl.
*A61F 11/06* (2006.01)

(52) U.S. Cl. .................................................... 381/71.11

(58) Field of Classification Search ............... 381/71.11, 381/71.14, 71.2, 71.8, 71.9, 71.12; 379/406.08; 708/322

See application file for complete search history.

(56) References Cited

U.S. PATENT DOCUMENTS 4,243,959 A 1/1981 Duttweiler
5,222,148 A 6/1993 Yuan
5,321,759 A 6/1994 Yuan
5,359,662 A * 10/1994 Yuan et al. ................. 381/71.14
5,386,472 A 1/1995 Pfaff et al.
5,418,857 A 5/1995 Eatwell et al.
5,475,761 A * 12/1995 Eatwell ...................... 381/71.11
5,586,190 A 12/1996 Trantow et al.
5,627,896 A 5/1997 Southward et al.
5,689,572 A 11/1997 Ohki et al.
5,694,474 A 12/1997 Ngo et al.
5,715,320 A 2/1998 Allie et al.
5,805,457 A 9/1998 Sanders
5,838,599 A 11/1998 Tao et al.
6,418,227 B1 7/2002 Kuo
6,449,586 B1 9/2002 Hoshuyama
7,110,554 B2 9/2006 Brennan et al.
7,426,464 B2 9/2008 Hui et al.
8,194,873 B2 6/2012 Pan et al.
2002/0172374 A1 11/2002 Bizjak
2003/0026438 A1 2/2003 Ray et al.
2005/0147258 A1 7/2005 Myllyla et al.
2005/0182336 A1 8/2005 Sippens Groenewegen
2007/0110254 A1 * 5/2007 Christoph et al. .............. 381/66
2007/0297619 A1 12/2007 Pan
2008/0095383 A1 4/2008 Pan et al.

(Continued)

FOREIGN PATENT DOCUMENTS

GB 2290635 A 1/1996

(Continued)

OTHER PUBLICATIONS

International Search Report and Written Opinion dated Dec. 15, 2009 for PCT/US2009/057945.

(Continued)

*Primary Examiner* — Robert Pascal
*Assistant Examiner* — Khiem Nguyen

(57) ABSTRACT

A method for determining leakage factors or adaptation rates, or both, for adaptive filters in an active noise reduction system. The leakage factor or adaptation rate, or both, may vary depending on a parameter of an input reference signal. The parameter may include one or more of reference signal input frequency, rate of change of reference input signal frequency, if a predetermined triggering condition exits, or if a predetermined event has occurred.

10 Claims, 12 Drawing Sheets

U.S. PATENT DOCUMENTS

| | | | |
|---|---|---|---|
| 2008/0273713 A1 | 11/2008 | Hartung et al. |
| 2008/0273714 A1 | 11/2008 | Hartung |
| 2010/0098263 A1 | 4/2010 | Pan et al. |
| 2010/0098265 A1 | 4/2010 | Pan et al. |
| 2010/0239105 A1 | 9/2010 | Pan |

FOREIGN PATENT DOCUMENTS

| | | | |
|---|---|---|---|
| WO | 9520841 | A1 | 8/1995 |
| WO | 01/73759 | A1 | 10/2001 |
| WO | 2008/002874 | A1 | 1/2008 |
| WO | 2008002873 | | 1/2008 |
| WO | 2009108396 | A1 | 9/2009 |

OTHER PUBLICATIONS

Anonymous: Active Engine Vibration Control with Variable A Method, Research Disclosure, Mason Publications, Hampshire, GB. vol. 345, No. 21. Jan. 1, 1993.

International Search Report and Written Opinion dated Feb. 6, 2008 for PCT/US2007/072026.

EP Search Report in Application PCT/US2007/072026 dated Feb. 6, 2008.

S.C. Douglas, "Performing Comparison of Two Implementations of the Leaky LMS Adaptive Filter," IEEE Trans. Signal Processing, vol. 45, 8, pp. 2125-2130, Aug. 1997.

S.J. Elliot, et al., "Effort Constraints in Adaptive Feedforward Control", IEEE Signal Processing Letters, vol. 3, No. 1, Jan. 1996, pp. 7-9.

S. J. Elliot, et al., Active Noise Control:, IEEE Signal Processing Magazine, Oct. 1993, pp. 12-35.

L. Hakansson, "The Filtered-x LMS Algorithim", Department if Telecomminications and Signal Processing, University of Kariskrona/Rooneby, 372 25 Ronneby, Sweden, Jan. 15, 2004.

B. Rigling, "Subspace Leaky LMS", IEEE Signal Processing Letters vol. 11, No. 2, Feb. 2004.

X. Qiu, et al. "A Study of time-domain FXLMS algorithms with control output constraint", Feb. 28, 2001, pp. 2815-2823.

T. Inoue, et al. "NV Countermeasure Technology for a Cylinder-On-Demand Engine-Development of Active Booming Noise Control System Applying Notich Filter", Copyright 2004, Honda R&D 04Annual-976.

International Preliminary Report on Patenability dated Sep. 12, 2008 for PCT/US07/072026.

International Search Report and Written Opinion dated Feb. 9, 2010 for PCT/US2009/057787.

Cartes David A. et al: "Experimental Evaluation of Leaky least-mean-square algorithms for active noise reduction in communication headsets". The Journal of the Acoustical Society of America, American Institute of Physics for the Acoustical Society of America, New York, NY, USA, vol. 111, No. 4, Apr. 1, 2002 pp. 1758-1771.

Gontijo, Walter A.: "FxLMS algorithm with Variable Step Size and Variable Leakage Factor for Active Vibration Control", Telecommunications Symposium, 2006 International, IEEE, PI, Sep. 1, 2006, pp. 572-575.

International Preliminary Report on Patentability dated May 10, 2010 for PCT/US2009/030268.

European Examination Report dated Feb. 23, 2009, for European Patent No. 07812302.3.

International Search Report and Written Opinion dated May 8, 2009 for PCT/US2009/030268.

Streeter A. D. et al.: Hybrid Feedforward-Feedback Active Noise Control, American Control Conference, 2004. Jun. 30-Jul. 2, 2004, Piscataway, NJ, IEEE.

European Examination Report dated Aug. 18, 2011, for European Application No. 07812302.3-2213.

2nd China Office Action dated Feb. 13, 2012 for application No. 200780022439.2.

CN Office Action dated Dec. 14, 2010 for CN Appln. 200780022439.2.

JP Office Action dated Aug. 9, 2011 for JP Appln. No. 2009518491.

CN Office Action dated Jun. 20, 2012 for CN Appln. No. 200980140810.4.

First Chinese Office Application dated Apr. 12, 2012 for CN Application No. 200980140809.1.

"Experimental Evaluation of Leaky Least-Mean-Square Algorithms for Active Noise Reduction in Communication Headsets," David A. Cartes et al, The Journal of the Acoustical Society of America, vol. 11, period. 4, pp. 1758-1771, 20020430, publishing date Apr. 30, 2002.

* cited by examiner

ACTIVE NOISE REDUCTION ADAPTIVE FILTER LEAKAGE ADJUSTING

BACKGROUND

This specification describes an active noise reduction system using adaptive filters and more particularly, a narrowband feed forward active noise reduction system. Active noise control using adaptive filters and narrowband feed forward active noise reduction systems are discussed generally in S. J. Elliot and P. A. Nelson, "Active Noise Control" IEEE Signal Processing Magazine, October 1993.

SUMMARY

In one aspect, a method for operating an active noise reduction system includes providing filter coefficients for an adaptive filter in response to a noise signal; determining leakage factors; smoothing the leakage factors to provide smoothed leakage factors; applying the smoothed leakage factors to the filter coefficients to provide modified filter coefficients; and applying the filter coefficients to an audio signal. The determining includes determining a leakage factor as a function of the frequency of an input reference signal. The applying may include multiplying an old filter coefficient value and a filter coefficient update amount by the smoothed leakage factors.

In another aspect, an active noise reduction system includes an adaptive filter, for providing an active noise reduction signal; a coefficient calculator, for providing filter coefficients for the adaptive filter; a leakage adjuster including a data smoother to provide smoothed leakage factors to apply to the filter coefficients, and further including circuitry to determine leakage factors as a function of the frequency of an input reference signal and to provide the leakage factors to the data smoother; and circuitry for applying the coefficients to an audio signal.

In another aspect, a method for operating an active noise reduction system includes providing filter coefficients of an adaptive filter in response to a noise signal and determining leakage factors associated with the filter coefficients. The determining includes in response to a first triggering condition, providing a first leakage factor; in response to a second triggering condition, providing a second leakage factor, different from the first leakage factor; and in the absence of the first triggering condition and the second triggering condition, providing a default leakage factor; and applying the filter coefficients to an audio signal. At least one of the providing the first leakage factor, providing the second leakage factor, and providing the third leakage factor includes determining the leakage factor value as a function of the frequency of a reference input signal.

In another aspect, a method includes determining a leakage factor for use in an adaptive filter of a noise reduction system as a function of the frequency of an input reference signal; applying the leakage factor to coefficients of the adaptive filter; and applying the coefficients to an audio signal. The method may further include applying the leakage factor to a filter coefficient update amount. The method may be incorporated in the operation of an active noise reduction system. The method may be incorporated in the operation of an active noise reduction system in a vehicle. The applying the leakage factor may include combining the adaptive filter coefficient value and the coefficient value update amount prior to the applying the leakage factor. The applying the leakage factor may include applying the leakage factor to the adaptive filter coefficient value to provide a modified adaptive filter coefficient value; applying the leakage factor to the coefficient value update amount to provide a modified coefficient value update amount; and combining the modified adaptive filter coefficient value and the modified coefficient value update amount.

Other features, objects, and advantages will become apparent from the following detailed description, when read in connection with the following drawing, in which:

DETAILED DESCRIPTION

Figure 1A:
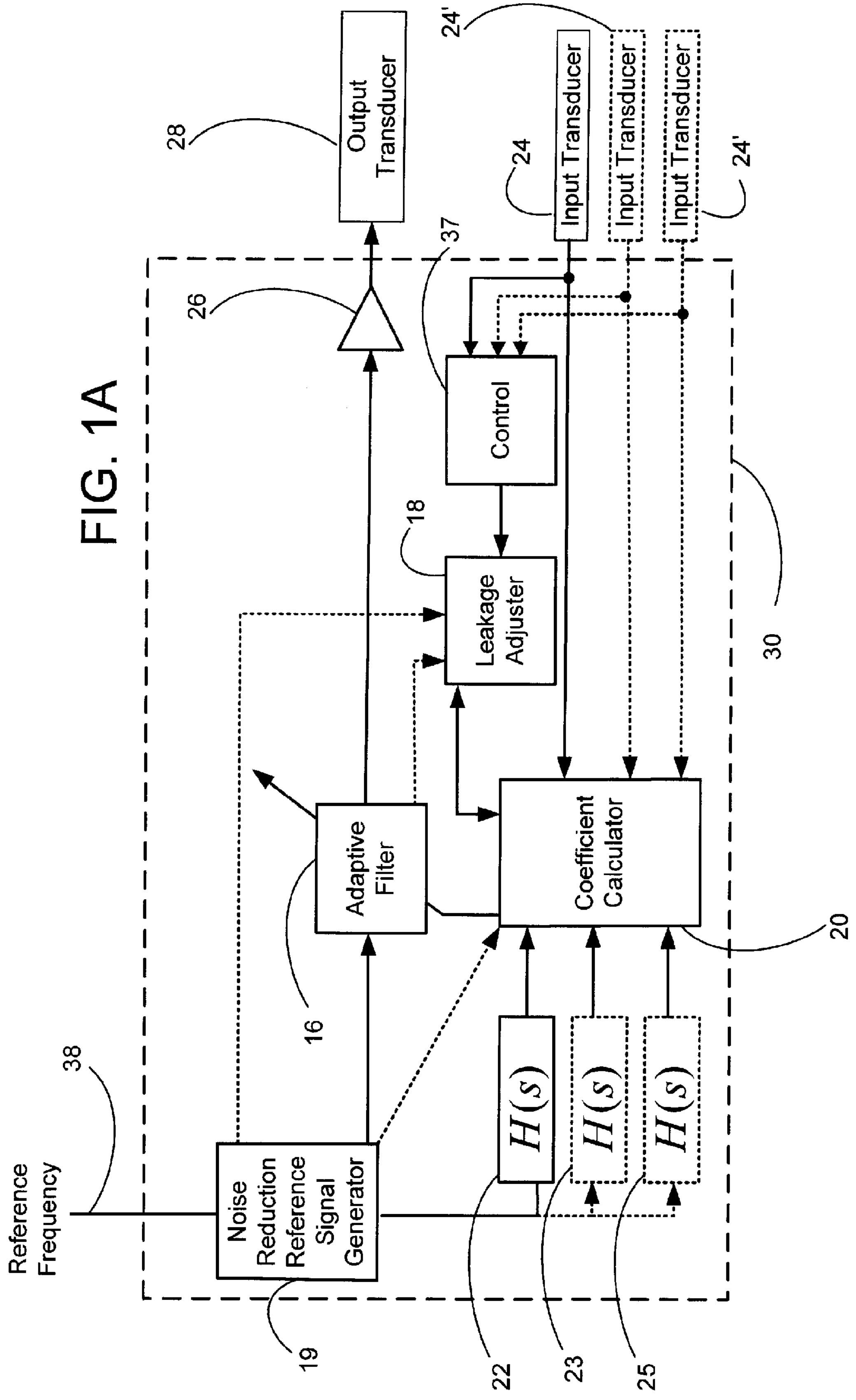
FIG. 1A is a block diagram of an active noise reduction system.

Though the elements of several views of the drawing may be shown and described as discrete elements in a block diagram and may be referred to as "circuitry", unless otherwise indicated, the elements may be implemented as one of, or a combination of, analog circuitry, digital circuitry, or one or more microprocessors executing software instructions. The software instructions may include digital signal processing (DSP) instructions. Unless otherwise indicated, signal lines may be implemented as discrete analog or digital signal lines. Multiple signal lines may be implemented as one discrete digital signal line with appropriate signal processing to process separate streams of audio signals, or as elements of a wireless communication system. Some of the processing operations may be expressed in terms of the calculation and application of coefficients. The equivalent of calculating and applying coefficients can be performed by other analog or DSP techniques and are included within the scope of this patent application. Unless otherwise indicated, audio signals may be encoded in either digital or analog form; conventional digital-to-analog and analog-to-digital converters may not be shown in circuit diagrams. This specification describes an active noise reduction system. Active noise reduction systems are typically intended to eliminate undesired noise (i.e. the goal is zero noise). However in actual noise reduction systems undesired noise is attenuated, but complete noise reduction is not attained. In this specification "driving toward zero" means that the goal of the active noise reduction system is zero noise, though it is recognized that the actual result is significant attenuation, not complete elimination.

Referring to FIG. 1A, there is shown a block diagram of an active noise reduction system. Communication path 38 is coupled to noise reduction reference signal generator 19 for presenting to the noise reduction reference signal generator a reference frequency. The noise reduction reference signal generator is coupled to filter 22 and adaptive filter 16. The filter 22 is coupled to coefficient calculator 20. Input transducer 24 is coupled to control block 37 and to coefficient calculator 20, which is in turn bidirectionally coupled to leakage adjuster 18 and adaptive filter 16. Adaptive filter 16 is coupled to output transducer 28 by power amplifier 26. Control block 37 is coupled to leakage adjuster 18. Optionally, there may be additional input transducers 24' coupled to coefficient calculator 20, and optionally, the adaptive filter 16 may be coupled to leakage adjuster 18. If there are additional input transducers 24', there typically will be a corresponding filter 23, 25. The optional logical couplings between the reference signal generator 19 and the coefficient calculator 20 and between the reference signal generator 19 and the leakage adjuster 18, both indicated by dashed lines, will be explained below.

In operation, a reference frequency, or information from which a reference frequency can be derived, is provided to the noise reduction reference signal generator 19. The noise reduction reference signal generator generates a noise reduction signal, which may be in the form of a periodic signal, such as a sinusoid having a frequency component related to the engine speed, to filter 22 and to adaptive filter 16. Input transducer 24 detects periodic vibrational energy having a frequency component related to the reference frequency and transduces the vibrational energy to a noise signal, which is provided to coefficient calculator 20. Coefficient calculator 20 determines coefficients for adaptive filter 16. Adaptive filter 16 uses the coefficients from coefficient calculator 20 to modify the amplitude and/or phase of the noise cancellation reference signal from noise reduction reference signal generator 19 and provides the modified noise cancellation signal to power amplifier 26. The noise reduction signal is amplified by power amplifier 26 and transduced to vibrational energy by output transducer 28. Control block 37 controls the operation of the active noise reduction elements, for example by activating or deactivating the active noise reduction system or by adjusting the amount of noise attenuation.

The adaptive filter 16, the leakage adjuster 18, and the coefficient calculator 20 operate repetitively and recursively to provide a stream of filter coefficients that cause the adaptive filter 16 to modify a signal that, when transduced to periodic vibrational energy, attenuates the vibrational energy detected by input transducer 24. Filter 22, which can be characterized by transfer function H(s), compensates for effects on the energy transduced by input transducer 24 of components of the active noise reduction system (including power amplifier 26 and output transducer 28) and of the environment in which the system operates.

Input transducer(s) 24, 24' may be one of many types of devices that transduce vibrational energy to electrically or digitally encoded signals, such as an accelerometer, a microphone, a piezoelectric device, and others. If there is more than one input transducer, 24, 24', the filtered inputs from the transducers may be combined in some manner, such as by averaging, or the input from one may be weighted more heavily than the others. Filter 22, coefficient calculator 20, leakage adjuster 18, and control block 37 may be implemented as instructions executed by a microprocessor, such as a DSP device. Output transducer 28 can be one of many electromechanical or electroacoustical devices that provide periodic vibrational energy, such as a motor or an acoustic driver.

Figure 1B:
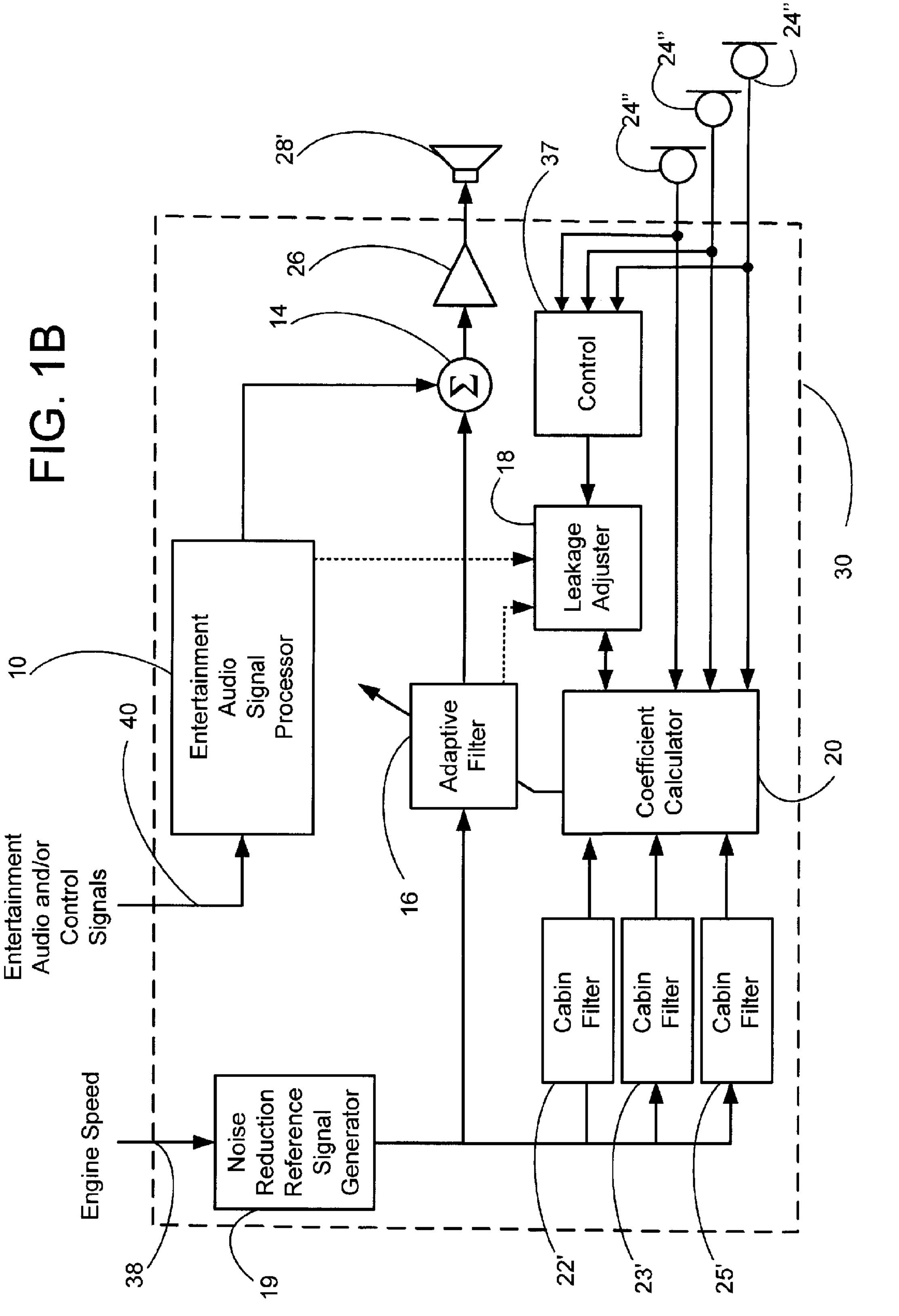
FIG. 1B is a block diagram including elements of the active noise reduction system of FIG. 1A implemented as an active acoustic noise reduction system in a vehicle.

Referring to FIG. 1B, there is shown a block diagram including elements of the active noise reduction system of FIG. 1A. The active noise reduction system of FIG. 1B is implemented as an active acoustic noise reduction system in an enclosed space. FIG. 1B is described as configured for a vehicle cabin, but and also may be configured for use in other enclosed spaces, such as a room or control station. The system of FIG. 1B also includes elements of an audio entertainment or communications system, which may be associated with the enclosed space. For example, if the enclosed space is a cabin in a vehicle, such as a passenger car, van, truck, sport utility vehicle, construction or farm vehicle, military vehicle, or airplane, the audio entertainment or communications system may be associated with the vehicle. Entertainment audio signal processor 10 is communicatingly coupled to signal line 40 to receive an entertainment audio signal and/or an entertainment system control signal, and is coupled to combiner 14 and may be coupled to leakage adjuster 18. Noise reduction reference signal generator 19 is communicatingly coupled to signal line 38 and to adaptive filter 16 and cabin filter 22', which corresponds to the filter 22 of FIG. 1A. Adaptive filter 16 is coupled to combiner 14, to coefficient calculator 20, and optionally may be directly coupled to leakage adjuster 18. Coefficient calculator 20 is coupled to cabin filter 22', to leakage adjuster 18, and to microphones 24", which correspond to the input transducers 24, 24' of FIG. 1A. Combiner 14 is coupled to power amplifier 26 which is coupled to acoustic driver 28', which corresponds to output transducer 28 of FIG. 1A. Control block 37 is communicatingly coupled to leakage adjuster 18 and to microphones 24". In many vehicles, entertainment audio signal processor 10 is coupled to a plurality of combiners 14, each of which is coupled to a power amplifier 26 and an acoustic driver 28'.

Each of the plurality of combiners 14, power amplifiers 26, and acoustic drivers 28' may be coupled, through elements such as amplifiers and combiners to one of a plurality of adaptive filters 16, each of which has associated with it a leakage adjuster 18, a coefficient calculator 20, and a cabin filter 22. A single adaptive filter 16, associated leakage adjuster 18, and coefficient calculator 20 may modify noise cancellation signals presented to more than one acoustic driver. For simplicity, only one combiner 14, one power amplifier 26, and one acoustic driver 28' are shown. Each microphone 24" may be coupled to more than one coefficient calculator 20.

All or some of the entertainment audio signal processor 10, the noise reduction reference signal generator 19, the adaptive filter 16, the cabin filter 22', the coefficient calculator 20 the leakage adjuster 18, the control block 37, and the combiner 14 may be implemented as software instructions executed by one or more microprocessors or DSP chips. The power amplifier 26 and the microprocessor or DSP chip may be components of an amplifier 30.

In operation, some of the elements of FIG. 1B operate to provide audio entertainment and audibly presented information (such as navigation instructions, audible warning indicators, cellular phone transmission, operational information [for example, low fuel indication], and the like) to occupants of the vehicle. An entertainment audio signal from signal line 40 is processed by entertainment audio signal processor 10. A processed audio signal is combined with an active noise reduction signal (to be described later) at combiner 14. The combined signal is amplified by power amplifier 26 and transduced to acoustic energy by acoustic driver 28'.

Some elements of the device of FIG. 1B operate to actively reduce noise in the vehicle compartment caused by the vehicle engine and other noise sources. The engine speed, which is typically represented as pulses indicative of the rotational speed of the engine, also referred to as revolutions per minute or RPM, is provided to noise reduction reference signal generator 19, which determines a reference frequency according to $$f(\text{Hz}) = \frac{\text{engine\_speed(rpm)}}{60}.$$

The reference frequency is provided to cabin filter 22'. The noise reduction reference signal generator 19 generates a noise cancellation signal, which may be in the form of a periodic signal, such as a sinusoid having a frequency component related to the engine speed. The noise cancellation signal is provided to adaptive filter 16 and in parallel to cabin filter 22'. Microphone 24" transduces acoustic energy, which may include acoustic energy corresponding to entertainment audio signals, in the vehicle cabin to a noise audio signal, which is provided to the coefficient calculator 20. The coefficient calculator 20 modifies the coefficients of adaptive filter 16. Adaptive filter 16 uses the coefficients to modify the amplitude and/or phase of the noise cancellation signal from noise reduction reference signal generator 19 and provides the modified noise cancellation signal to signal combiner 14. The combined effect of some electro-acoustic elements (for example, acoustic driver 28', power amplifier 26, microphone 24" and of the environment within which the noise reduction system operates) can be characterized by a transfer function H(s). Cabin filter 22' models and compensates for the transfer function H(s). The operation of the leakage adjuster 18 and control block 37 will be described below.

The adaptive filter 16, the leakage adjuster 18, and the coefficient calculator 20 operate repetitively and recursively to provide a stream of filter coefficients that cause the adaptive filter 16 to modify an audio signal that, when radiated by the acoustic driver 28', drives the magnitude of specific spectral components of the signal detected by microphone 24" to some desired value. The specific spectral components typically correspond to fixed multiples of the frequency derived from the engine speed. The specific desired value to which the magnitude of the specific spectral components is to be driven may be zero, but may be some other value as will be described below.

The elements of FIGS. 1A and 1B may also be replicated and used to generate and modify noise reduction signals for more than one frequency. The noise reduction signal for the other frequencies is generated and modified in the same manner as described above.

The content of the audio signals from the entertainment audio signal source includes conventional audio entertainment, such as for example, music, talk radio, news and sports broadcasts, audio associated with multimedia entertainment and the like, and, as stated above, may include forms of audible information such as navigation instructions, audio transmissions from a cellular telephone network, warning signals associated with operation of the vehicle, and operational information about the vehicle. The entertainment audio signal processor may include stereo and/or multi-channel audio processing circuitry. Adaptive filter 16 and coefficient calculator 20 together may be implemented as one of a number of filter types, such as an n-tap delay line; a Laguerre filter; a finite impulse response (FIR) filter; and others. The adaptive filter may use one of a number of types of adaptation schemes, such as a least mean squares (LMS) adaptive scheme; a normalized LMS scheme; a block LMS scheme; or a block discrete Fourier transform scheme; and others. The combiner 14 is not necessarily a physical element, but rather may be implemented as a summation of signals.

Though shown as a single element, the adaptive filter 16 may include more than one filter element. In some embodiments of the system of FIG. 1B, adaptive filter 16 includes two FIR filter elements, one each for a sine function and a cosine function with both sinusoid inputs at the same frequency, each FIR filter using an LMS adaptive scheme with a single tap, and a sample rate which may be related to the audio frequency sampling rate r (for example $$\frac{r}{28}).$$

Suitable adaptive algorithms for use by the coefficient calculator 20 may be found in *Adaptive Filter Theory*, *4th Edition* by Simon Haykin, ISBN 0130901261. Leakage adjuster 18 will be described below.

Figure 2A:
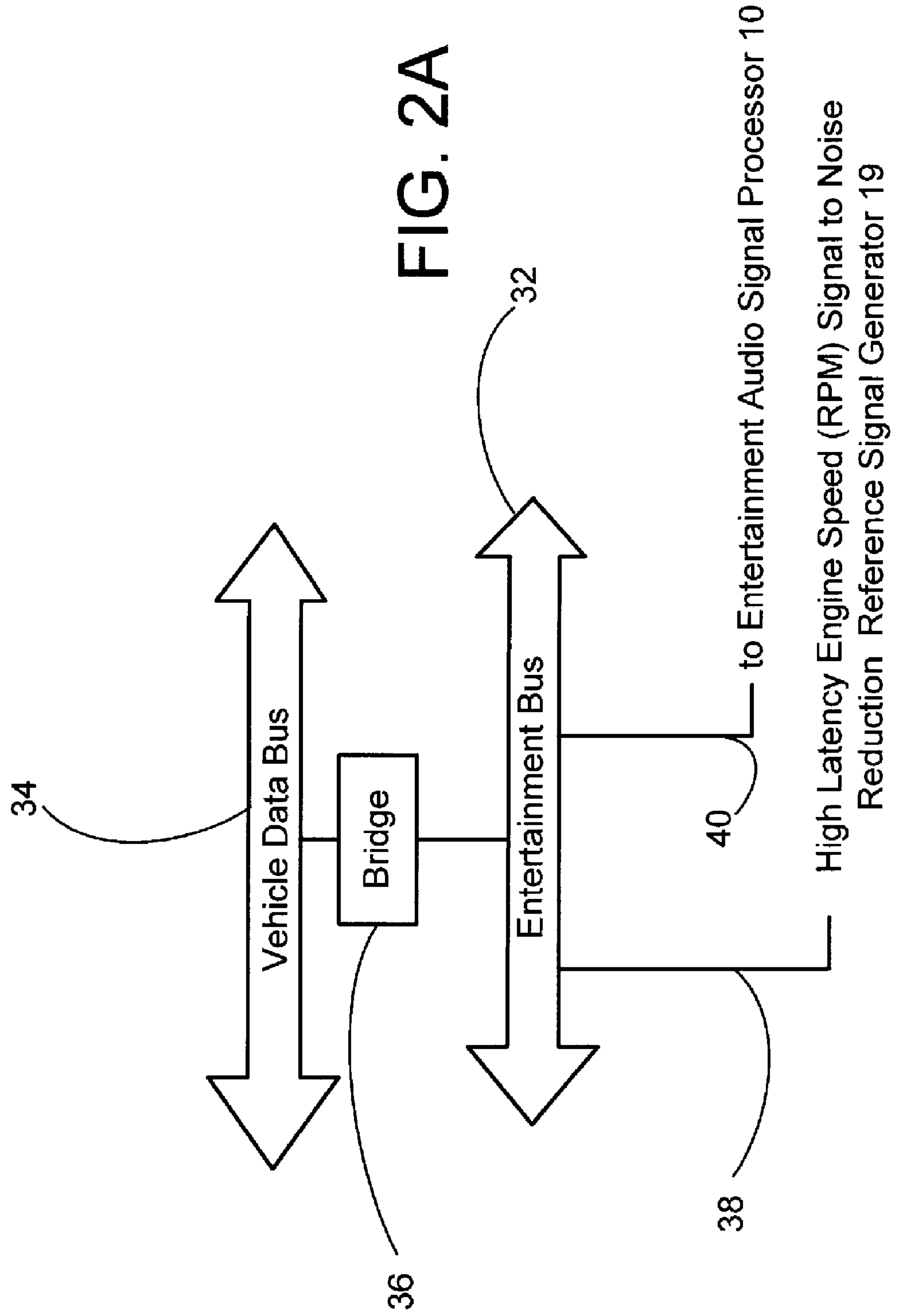
FIG. 2A is a block diagram of a delivery system of the reference frequency and an implementation of the delivery system of the entertainment audio signal of FIG. 1B.

FIG. 2A is a block diagram showing devices that provide the engine speed to noise reduction reference signal generator 19 and that provide the audio entertainment signal to audio signal processor 10. The audio signal delivery elements may include an entertainment bus 32 coupled to audio signal processor 10 of FIG. 1B by signal line 40 and further coupled to noise reduction reference signal generator 19 by signal line 38. The entertainment bus may be a digital bus that transmits digitally encoded audio signals among elements of a vehicle audio entertainment system. Devices such as a CD player, an MP3 player, a DVD player or similar devices or a radio receiver (none of which are shown) may be coupled to the entertainment bus 32 to provide an entertainment audio signal. Also coupled to entertainment bus 32 may be sources of audio signals representing information such as navigation instructions, audio transmissions from a cellular telephone network, warning signals associated with operation of the vehicle, and other audio signals. The engine speed signal delivery elements may include a vehicle data bus 34 and a bridge 36 coupling the vehicle data bus 34 and the entertainment bus 32. The example has been described with reference to a vehicle with an entertainment system; however the system of FIG. 2A may be implemented with noise reducing systems associated with other types of sinusoidal noise sources, for example a power transformer. The system may also be implemented in noise reducing systems that do not include an entertainment system, by providing combinations of buses, signal lines, and other signal transmission elements that result in latency characteristics similar to the system of FIG. 2A.

In operation, the entertainment bus 32 transmits audio signals and/or control and/or status information for elements of the entertainment system. The vehicle data bus 34 may communicate information about the status of the vehicle, such as the engine speed. The bridge 36 may receive engine speed information and may transmit the engine speed information to the entertainment bus, which in turn may transmit a high latency engine speed signal to the noise reduction reference signal generator 19. As will be described more fully below, in FIGS. 2A and 2B, the terms "high latency" and "low latency" apply to the interval between the occurrence of an event, such as a change in engine speed, and the arrival of an information signal indicating the change in engine speed at the active noise reduction system. The buses may be capable of transmitting signals with low latency, but the engine speed signal may be delivered with high latency, for example because of delays in the bridge 36.

Figure 2B:
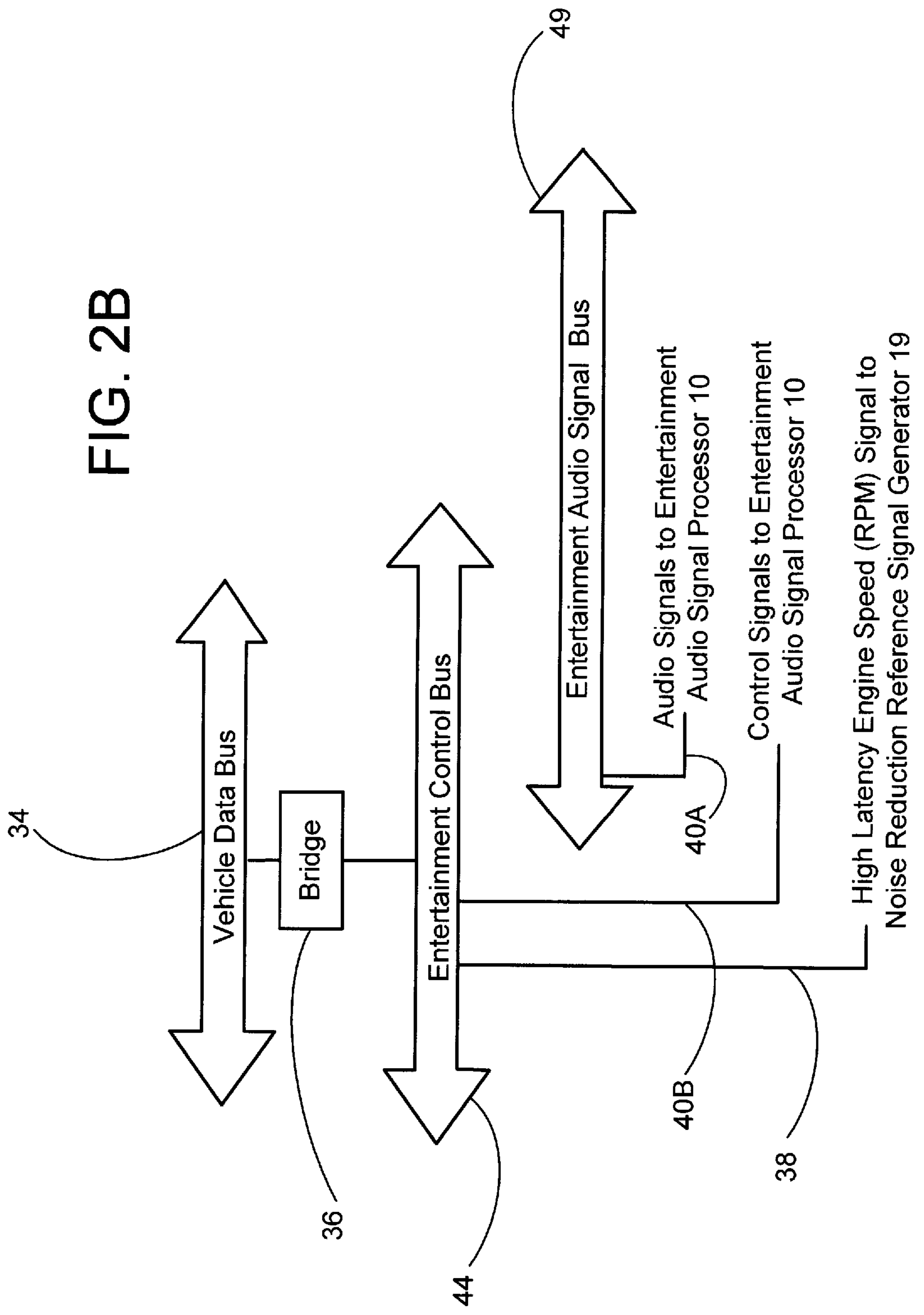
FIG. 2B is a block diagram of another implementation of the delivery system of the reference frequency and the delivery system of the entertainment audio signal of FIG. 1B.

FIG. 2B illustrates another implementation of the signal delivery elements of the engine speed signal and the signal delivery elements of the entertainment audio signal of FIG. 1B. The entertainment audio signal delivery elements include entertainment audio signal bus 49 coupled to audio signal processor 10 of FIG. 1B by signal line 40A. Entertainment control bus 44 is coupled to audio entertainment processor 10 of FIG. 1B by signal line 40B. The engine speed signal delivery elements include the vehicle data bus 34 coupled to an entertainment control bus 44 by bridge 36. The entertainment control bus 44 is coupled to noise reduction reference signal generator 19 by signal line 38.

The embodiment of FIG. 2B operates similarly to the embodiment of FIG. 2A, except that the high latency engine speed signal is transmitted from the bridge 36 to the entertainment control bus 44 and then to the noise reduction reference signal generator 19. Audio signals are transmitted from the entertainment audio signal bus 49 to entertainment audio signal processor 10 over signal line 40A. Entertainment control signals are transmitted from entertainment control bus 44 to entertainment audio signal processor 10 of FIG. 1 by signal line 40B. Other combinations of vehicle data buses, entertainment buses, entertainment control buses, entertainment audio signal buses, and other types of buses and signal lines, depending on the configuration of the vehicle, may be used to provide the engine speed signal to reference signal generator 19 and the audio entertainment signal to entertainment signal processor 20.

Conventional engine speed signal sources include a sensor, sensing or measuring some engine speed indicator such as crankshaft angle, intake manifold pressure, ignition pulse, or some other condition or event. Sensor circuits are typically low latency circuits but require the placement of mechanical, electrical, optical or magnetic sensors at locations that may be inconvenient to access or may have undesirable operating conditions, for example high temperatures, and also require communications circuitry, typically a dedicated physical connection, between the sensor and noise reduction reference signal generator 19 and/or adaptive filter 16 and/or cabin filter 22'. The vehicle data bus is typically a high speed, low latency bus that includes information for controlling the engine or other important components of the vehicle. Interfacing to the vehicle data bus adds complexity to the system, and in addition imposes constraints on the devices that interface to the vehicle data bus so that the interfacing device does not interfere with the operation of important components that control the operation of the vehicle. Engine speed signal delivery systems according to FIGS. 2A and 2B are advantageous over other engine speed signal sources and engine speed signal delivery systems because they permit active noise reduction capability without requiring any dedicated components such as dedicated signal lines. Arrangements according to FIGS. 2A and 2B are further advantageous because the vehicle data bus 34, bridge 36, and one or both of the entertainment bus 32 of FIG. 2A or the entertainment control bus 44 of FIG. 2B are present in many vehicles so no additional signal lines for engine speed are required to perform active noise reduction. Arrangements according to FIG. 2A or 2B also may use existing physical connection between the entertainment bus 32 or entertainment control bus 44 and the amplifier 30 and require no additional physical connections, such as pins or terminals for adding active noise reduction capability. Since entertainment bus 32 or entertainment control bus 44 may be implemented as a digital bus, the signal lines 38 and 40 of FIG. 2A and signal lines 38, 40A and 40B of FIG. 2B may be implemented as a single physical element, for example a pin or terminal, with suitable circuitry for routing the signals to the appropriate component.

An engine speed signal delivery system according to FIGS. 2A and 2B may be a high latency delivery system, due to the bandwidth of the entertainment bus, the latency of the bridge 36, or both. "High latency," in the context of this specification, means a latency between the occurrence of an event, such as an ignition event or a change in engine speed, and the arrival at noise reduction reference signal generator 19 of a signal indicating the occurrence of the event, of 10 ms or more.

An active noise reduction system that can operate using a high latency signal is advantageous because providing a low latency signal to the active noise reduction system is typically more complicated, difficult, and expensive than using an already available high latency signal.

Figure 3A:
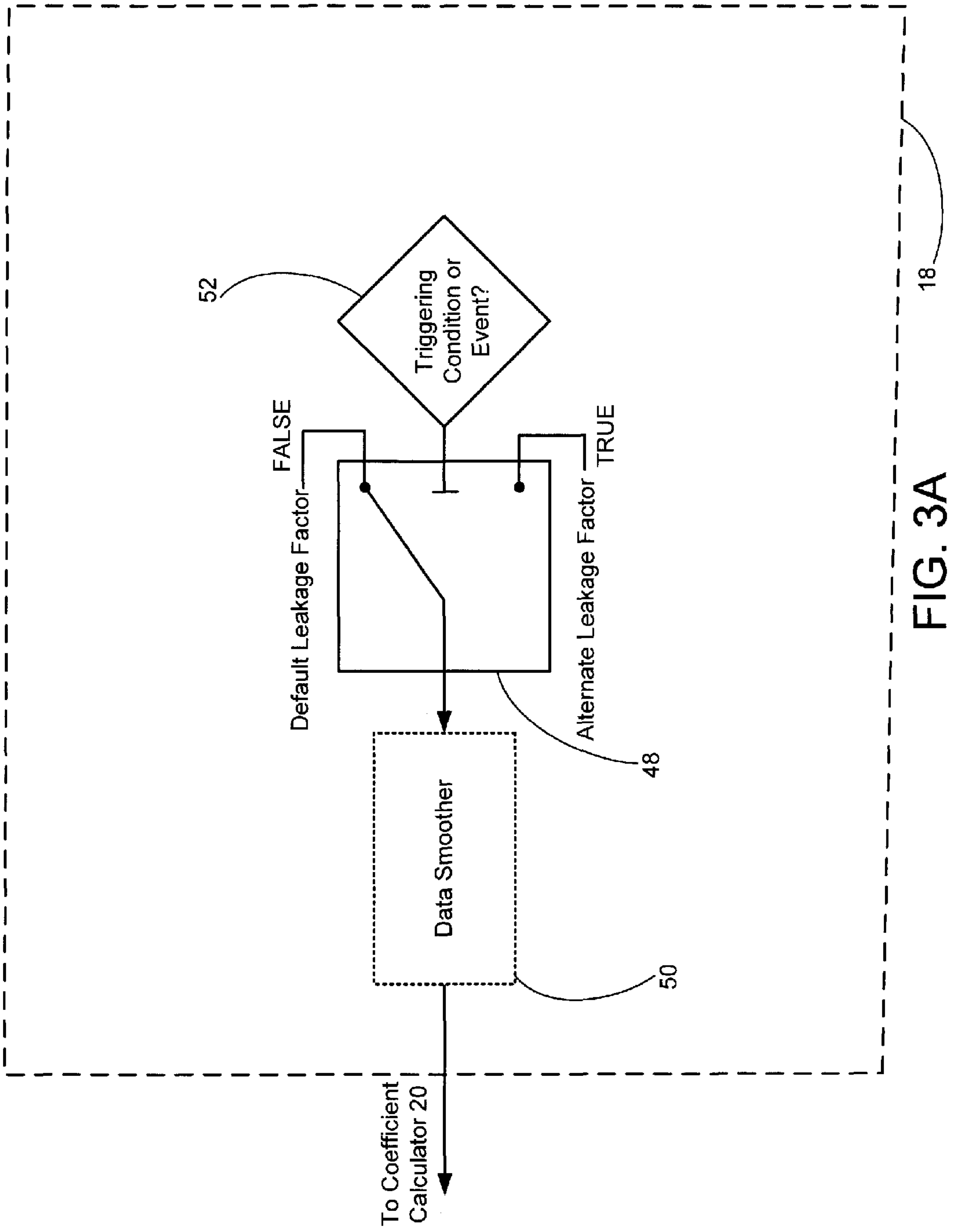
FIG. 3A is a block diagram showing the logical flow of the operation of the leakage adjuster of FIGS. 1A and 1B.

The leakage adjuster 18 will now be described in more detail. FIG. 3A is a block diagram showing the logical flow of the operation of the leakage adjuster 18. The leakage adjuster selects a leakage factor to be applied by the coefficient calculator 20. A leakage factor is a factor α applied in adaptive filters to an existing coefficient value when the existing coefficient value is updated by an update amount; for example $$(\text{new\_value})=\alpha(\text{old\_value})+(\text{update\_amount})$$

Information on leakage factors may be found in Section 13.2 of *Adaptive Filter Theory* by Simon Haykin, $4^{th}$ Edition, ISBN 0130901261. Logical block 52 determines if a predefined triggering event has occurred, or if a predefined triggering condition exists, that may cause it to be desirable to use an alternate leakage factor. Specific examples of events or conditions will be described below in the discussion of FIG. 3E. If the value of the logical block 52 is FALSE, the default leakage factor is applied at leakage factor determination logical block 48. If the value of logical block 52 is TRUE, an alternate, typically lower, leakage factor may be applied at leakage factor determination logical block 48. The alternate leakage factor may be calculated according to an algorithm, or may operate by selecting a leakage factor value from a discrete number of predetermined leakage factor values based on predetermined criteria. The stream of leakage factors may optionally be smoothed (block 50), for example by low pass filtering, to prevent abrupt changes in the leakage factor that have undesirable results. The low pass filtering causes leakage factor applied by adaptive filter 16 to be bounded by the default leakage factor and the alternate leakage factor. Other forms of smoothing may include slew limiting or averaging over time.

As stated above, the leakage factor α may be applied to the coefficient updating process according to $$(\text{new\_value})=\alpha(\text{old\_value})+(\text{update\_amount})$$

In one embodiment, the leakage factor α is applied to the coefficient updating process as $$(\text{new\_value})=\alpha((\text{old\_value})+(\text{update\_amount}))$$

In this embodiment, the leakage factor is applied not only to the old value, but also to the update amount.

One advantage of the alternate method of applying the leakage factor is that the adaptive filter may be more well-behaved in some pathological cases, for example if a user disables the filter because the user does not want noise cancellation or if the input transducer detects an impulse type vibrational energy.

Another advantage of the alternate method of applying the leakage factor is that changes in the leakage factor do not affect the phase of the output. The type of adaptive filter 16 typically used for suppressing sinusoidal noise, for example vehicle engine noise, is typically a single frequency adaptive notch filter. A single frequency adaptive notch filter includes two single coefficient adaptive filters, one for the cosine term and one for the sine term:

$S(n)=w1(n)\sin(n)+w2(n)\cos(n)=|S(n)|\sin(n+ang(S(n)))$ where S(n) is the net output of the adaptive filter 16, w1(n) is the new value of the filter coefficient of the sine term adaptive filter, w2(n) is the new value of the filter coefficient of the cosine term adaptive filter, |S(n)| is the magnitude of S(n), which is equal to $\sqrt{(w1(n))^2+(w2(n))^2}$, and ang(S(n)) is the angle of S(n), which is $$= \arctan\left(\frac{w2(n)}{w1(n)}\right).$$

With the other method of application of the leakage factor, $$ang(S(n)) = \arctan\frac{\alpha w2(n-1) + \text{update\_amount2}}{\alpha w1(n-1) + \text{update\_amount1}}$$

(where w1(n−1) is the old value of the filter coefficient of the sine term adaptive filter, w2(n−1) is the old value of the cosine term adaptive filter, update_amount1 is the update amount of the sine term adaptive filter and update_amount2 is the update amount of the cosine term adaptive filter), so that the angle of S(n) is dependent on the leakage factor α. With the alternate method of applying the leakage factor, $$ang(S(n)) = \arctan\frac{\alpha(w2(n-1) + \text{update\_amount2})}{\alpha(w1(n-1) + \text{update\_amount1})} = \arctan\frac{\alpha w2(n)}{\alpha w1(n)}.$$

The leakage factors in the numerator and denominator can be factored out so that $$ang(S(n)) = \arctan\frac{w2(n)}{w1(n)},$$

so that angS(n) is independent of the leakage term and changes in leakage factor do not affect the phase of the output.

Figure 3B:
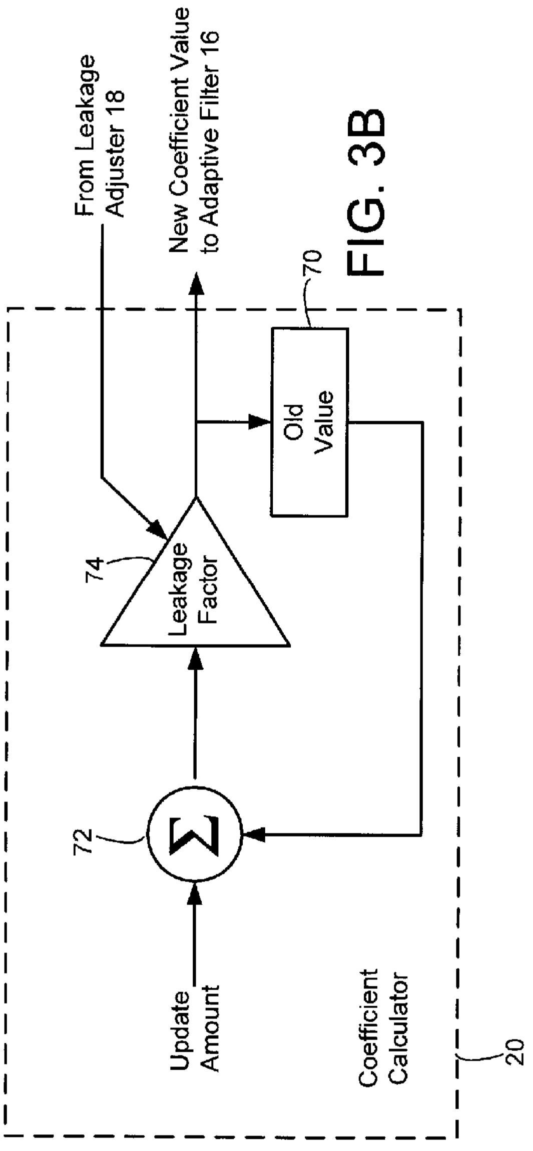
FIGS. 3B and 3C are block diagrams showing the logical flow of an application of a leakage factor to an update amount and an old coefficient value.
Figure 3C:
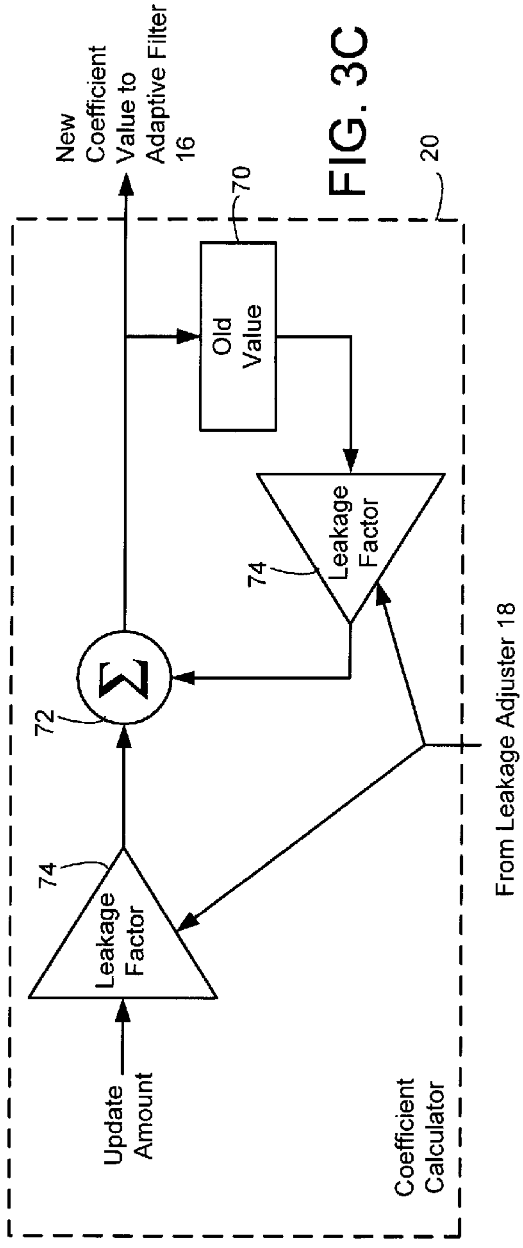

Logically, the application of the leakage factor value can be done in at least two ways. In FIG. 3B, the delayed new coefficient value becomes the old filter coefficient value (represented by block 70) for the next iteration and is summed at summer 72 with the update amount prior to the application of the leakage factor value (represented by multiplier 74). In FIG. 3C, the leakage factor is applied (represented by multipliers 74) separately to the delayed new coefficient value which becomes the old filter coefficient value (represented by block 70) and to the filter coefficient value update amount separately. The leakage factor modified old filter coefficient value and the leakage factor modified filter coefficient update amount are then combined (represented by summer 72) to form the new coefficient value, which is delayed and becomes the old filter coefficient value for the next iteration.

Figure 3D:
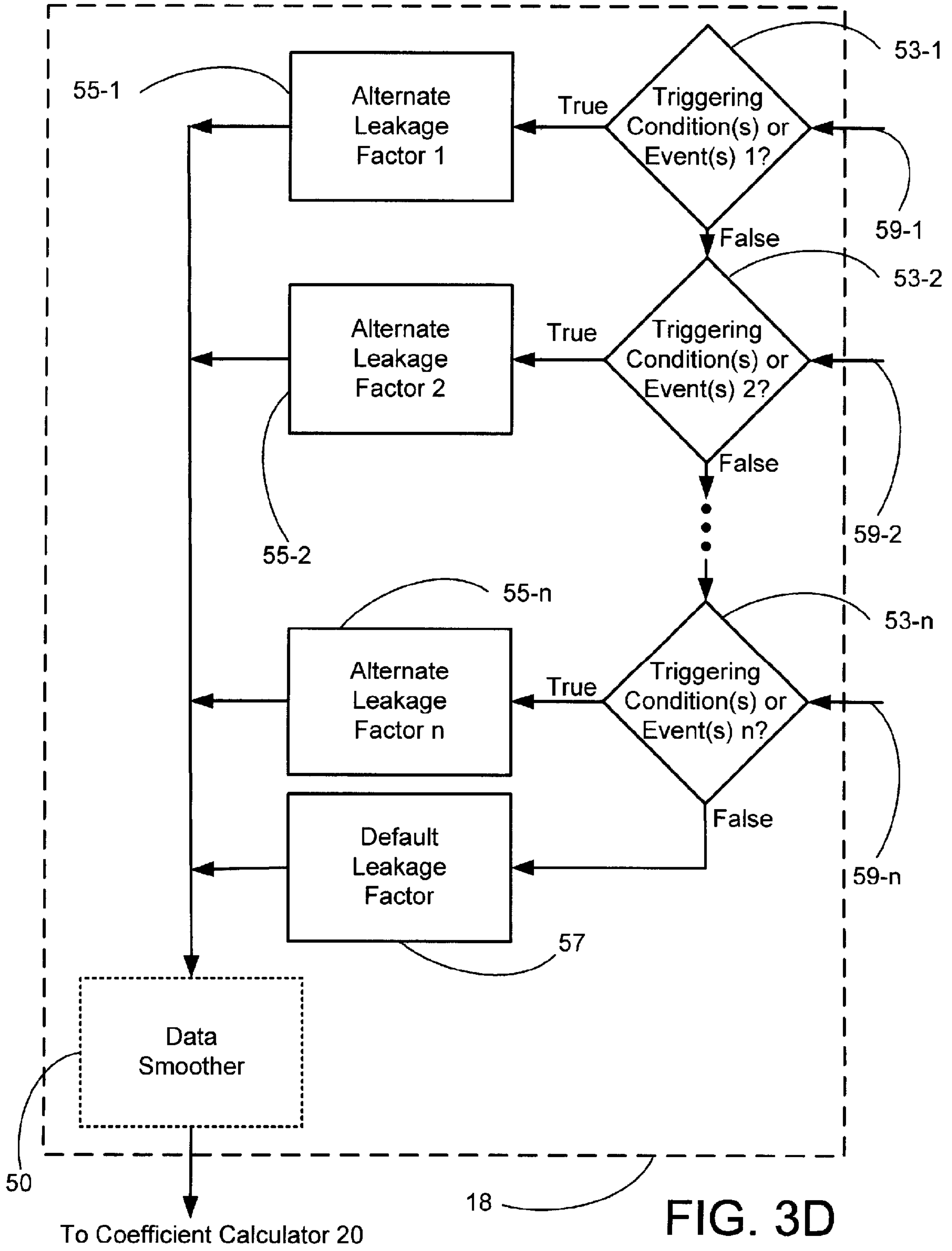
FIGS. 3D and 3E are block diagrams showing the logical flow of the operation of another implementation of a leakage adjuster, permitting a more complex leakage adjustment scheme.

FIG. 3D is a block diagram showing the logical flow of the operation of a leakage adjuster 18 permitting more than one, for example n, alternate leakage factor and permitting the n alternate leakage factors to be applied according to a predetermined priority. At logical block 53-1, it is determined if the highest priority triggering conditions exist or events have occurred. If the value of logical block 53-1 is TRUE, the leakage factor associated with the triggering conditions and events of logical block 53-1 is selected at logical block 55-1 and provided to the coefficient calculator 20 through a data smoother 50, if present. If the value of logical block 53-1 is FALSE, it is determined at logical block 53-2 if the second highest priority triggering conditions exist or events have occurred. If the value of logical block 53-2 is TRUE, the leakage factor associated with the triggering conditions and events of logical block 53-2 is selected at logical block 55-2 and provided to the coefficient calculator 20 through the data smoother 50, if present. If the value of logical block 53-2 is FALSE, then it is determined if the next highest priority triggering conditions exist or events have occurred. The process proceeds until, at logical block **53-*n*, it is determined if the lowest (or nth highest) priority triggering conditions exist or events have occurred. If the value of logical block 53-*n* is TRUE, the leakage factor associated with the lowest priority triggering conditions or events is selected at logical block 55-*n* and provided to the coefficient calculator 20 through the data smoother 50, if present. If the value of logical block 53-*n* is FALSE, at logical block 57 the default leakage factor is selected and provided to the coefficient calculator 20 through the data smoother 50**, if present.

In one implementation of FIG. 3D, there are 2 sets of triggering conditions and events and two associated leakage factors (n=2). The highest priority triggering conditions or events include the system being deactivated, the frequency of the noise reduction signal being out of the spectral range of the acoustic driver, or the noise detected by an input transducer such as a microphone having a magnitude that would induce non-linear operation, such as clipping. The leakage factor associated with the highest priority triggering conditions is 0.1. The second highest priority triggering conditions or events include the cancellation signal magnitude from adaptive filter 16 exceeding a threshold magnitude, the magnitude of the entertainment audio signal approaching (for example coming within a predefined range, such as 6 dB) the signal magnitude at which one of more electro-acoustical elements of FIG. 1B, such as the power amplifier 26 or the acoustic driver 28' may operate non-linearly, or some other event occurring that may result in an audible artifact, such as a click or pop, or distortion. Events that may cause an audible artifact, such as a click, pop, or distortion may include output levels being adjusted or the noise reduction signal having an amplitude or frequency that is known to cause a buzz or rattle in the acoustic driver 28 or some other component of the entertainment audio system. The leakage factor associated with the second highest priority triggering conditions and events is 0.5. The default leakage factor is 0.999999.

Figure 3E:
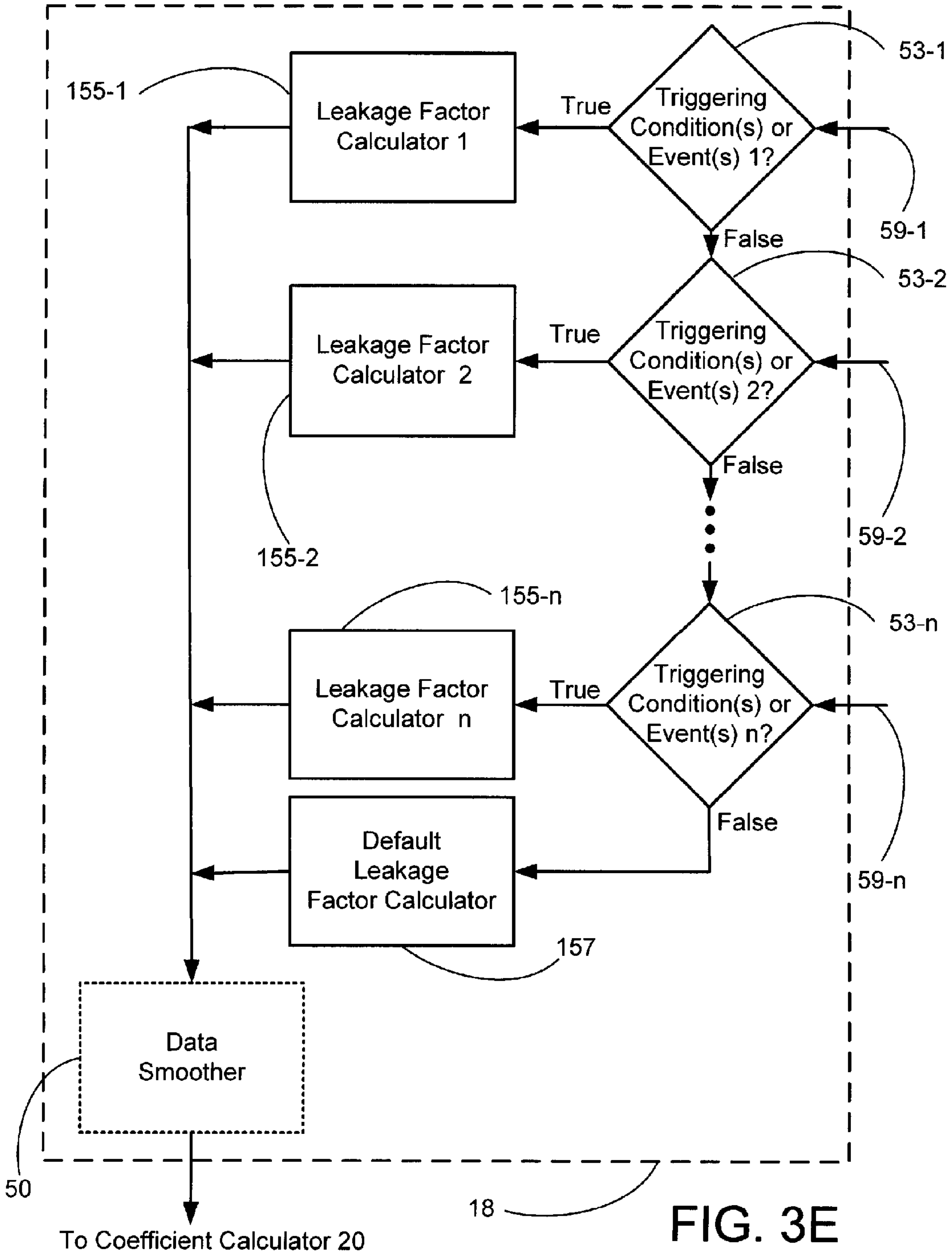

FIG. 3E shows another implementation of the leakage adjuster of FIG. 3D. In the leakage adjuster of FIG. 3E, the alternate leakage factors at blocks **55-1-55-*n* of FIG. 3D are replaced by leakage factor calculators 155-1 through 155-*n* and the default leakage factor block 57 of FIG. 3B is replaced by a default leakage factor calculator 157. The leakage factor calculators permit the default leakage factor and/or the alternate leakage factors to have a range of values instead of a single value and further permit the leakage factor to be dependent on the triggering condition or on some other factor. The specific leakage factor applied may be selected from a set of discrete values (for example from a look-up table), or may be calculated, based on a defined mathematical relationship with an element of the triggering condition, with a filter coefficient, with the cancellation signal magnitude, or with some other condition or measurement. For example, if the triggering condition is the cancellation signal magnitude from adaptive filter 16 exceeding a threshold magnitude, the leakage factor could be an assigned value. If the triggering condition is FALSE, the default leakage could be $\alpha_{default}=\alpha_{base}+\lambda A$, where $\alpha_{base}$ is a base leakage value, A is the amplitude of the cancellation signal, and $\lambda$ is a number representing the slope (typically negative) of a linear relationship between the default leakage factor and the amplitude of the cancellation signal. In other examples, the leakage factor may be determined according to a nonlinear function, for example a quadratic or exponential function, or in other examples, the slope may be zero, which is equivalent to the implementation of FIG. 3**B, in which the default and alternate leakage factors have set values.

Elements of the implementations of FIGS. 3D and 3E may be combined. For example, some of the alternate leakage factors may be predetermined and some may be calculated; some or all of the alternate leakage factors may be predetermined and the default leakage factor may be calculated; some or all of the alternate leakage factors may be predetermined and the default leakage factor may be calculated; and so forth.

A leakage factor adjuster according to FIG. 3E may force a lower energy solution.

Logical blocks 53-1-53-*n* receive indication that a triggering event has or is about to occur or that a triggering condition exists from an appropriate element of FIG. 1A or 1B, as indicated by arrows 59-1-59-*n*. The appropriate element may be control block 37 of FIG. 1B; however the indication may come from other elements. For example if the predefined event is that the magnitude of the entertainment audio signal approaches a non-linear operating range of one of the elements of FIG. 1B, the indication may originate in the entertainment audio signal processor 10 (not shown in this view).

In another example, the predefined event is that the reference frequency is near a frequency at which the system is deactivated, for example due to limitations of one of the of the output transducers 28, or to prevent a listener from localizing on one of the transducers, a high reference frequency, short wavelength reference signal that could result in lack of correlation between the noise at the listener's ear and the microphone, or some other reason. In this instance, the leakage factor may be set to allow the filter coefficients to decrease in value at a slower rate than in normal operation to improve the system performance for input signals that dwell near a deactivation frequency and fluctuate above and below the deactivation frequency. In this example, a leakage factor of 0.5 may be appropriate when the predefined event is that the reference frequency is near a frequency at which the system is deactivated. In this example, the leakage adjuster 18 may receive the reference frequency from noise reduction reference signal generator as indicated by the dashed line in FIG. 1A. Other possible predefined events include a rapid change in the frequency of the input signal.

The processes and devices of FIGS. 3A, 3D, and 3E are typically implemented by digital signal processing instructions on a DSP processor. Specific values for the default leakage factor and the alternate leakage factor may be determined empirically. Some systems may not apply a leakage factor in default situations. Since the leakage factor is multiplicative, not applying a leakage factor is equivalent to applying a leakage factor of 1. Data smoother 50 may be implemented, for example as a first order low pass filter with a tunable frequency cutoff that may be set, for example, at 20 Hz.

An active noise reduction system using the devices and methods of FIGS. 1A, 1B, 3A, 3D, and 3E is advantageous because it significantly reduces the number of occurrences of audible clicks or pops, and because it significantly reduces the number of occurrences of distortion and nonlinearities. Another method for reducing the occurrences of audible clicks or pops and reducing the number of occurrences of distortion and nonlinearities is to modify the adaptation rate of the adaptive filter.

As stated above, the coefficient updating process proceeds according to $$(new\_value)=\alpha(old\_value)+(update\_amount)$$

or $$(new\_value)=\alpha((old\_value)+(update\_amount)).$$

The value of update_amount is update_amount=$\mu x_n e_n$, where $x_n$, is the reference input to the filter, $e_n$, is the error signal to be minimized, and $\mu$ is the adaptation rate or gain. The factor $x_n$ is provided in the form of a sine wave from noise reduction reference signal generator 19. The error signal $e_n$ is provided by the input transducer 24. The value of the adaptation rate $\mu$ determines how quickly the filter converges. A high adaptation rate allows the filter to converge quickly, but risks instability. A low adaptation rate causes the filter to converge less quickly, but is less prone to instability. Therefore, it may be appropriate to provide a process for controlling the adaptation rate, based on operating conditions of the vehicle.

Figure 4A:
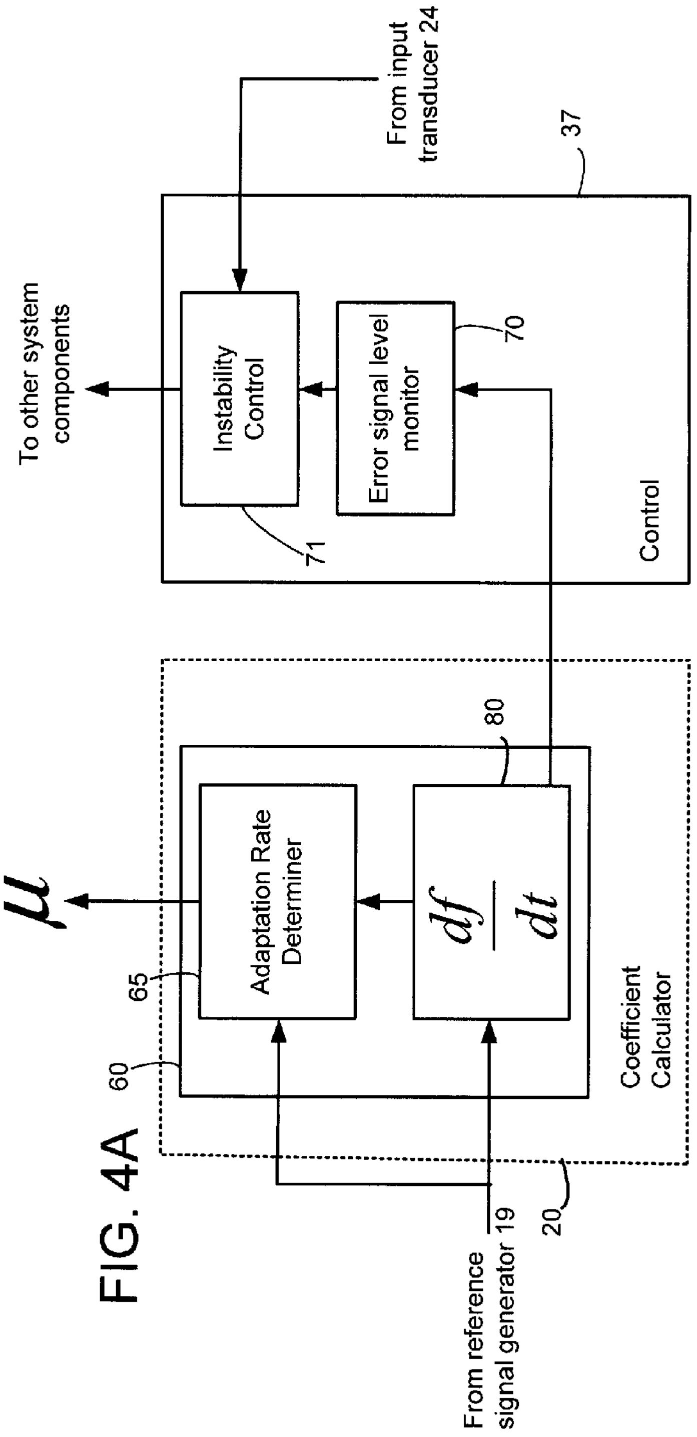
FIG. 4A is a block diagram showing some details of a coefficient calculator and a control block.
Figure 4B:
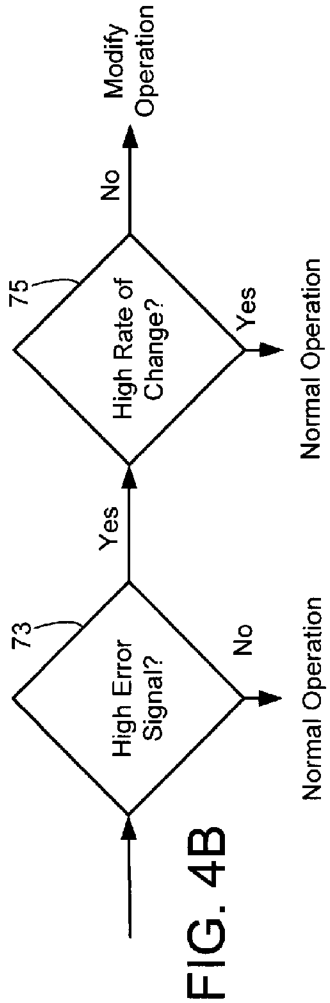
FIG. 4B is a block diagram showing the logical flow of the error signal monitor and the instability control block.

A logical arrangement for determining the adaptation rate is shown in FIG. 4A. The adaptation rate module 60 receives inputs that provide it with the data that it needs to determine the adaptation rate. In this example, the data needed is frequency-related, for example the frequency of the reference input signal from the noise reduction reference signal generator 19. The adaptation rate determiner 65 may manipulate the frequency-related input, for example by determining the rate of change of the reference input signal, as indicated by rate of change block 80. FIG. 4B and the other elements of FIG. 4A will be explained below.

Figure 5A:
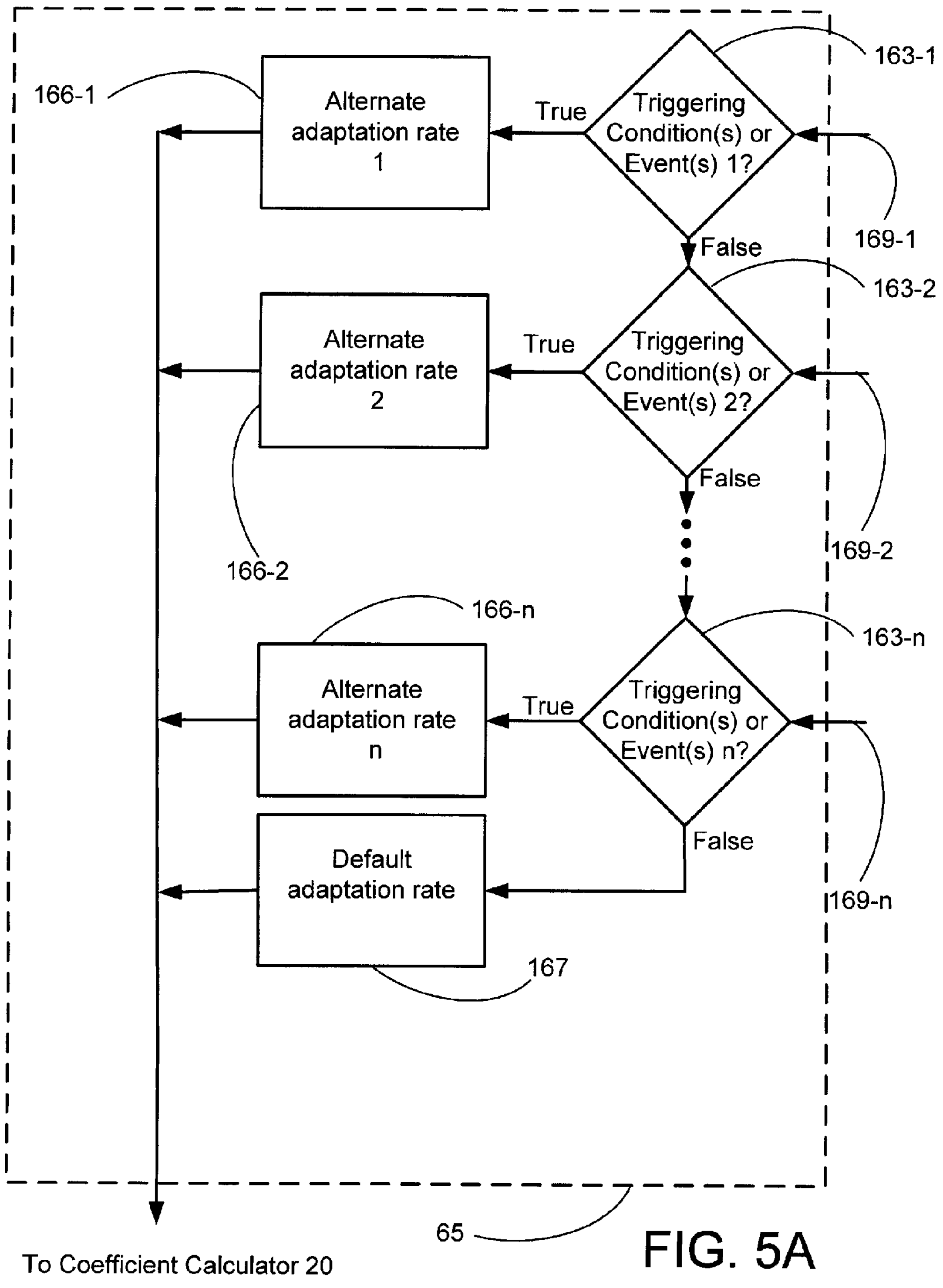
FIGS. 5A and 5B are block diagrams illustrating the logical flow of the operation of an adaptation rate determiner.

FIG. 5A is a block diagram showing the logical flow of the operation of an adaptation rate determiner 65 permitting more than one, for example n, alternate adaptation rates and permitting the n alternate adaptation rates to be applied according to a predetermined priority. At logical block 163-1, it is determined if the highest priority triggering conditions exist or events have occurred. If the value of logical block 163-1 is TRUE, the adaptation rate associated with the triggering conditions and events of logical block 163-1 is selected at logical block 166-1 and provided to the coefficient calculator 20. If the value of logical block 163-1 is FALSE, it is determined at logical block 163-2 if the second highest priority triggering conditions exist or events have occurred. If the value of logical block 163-2 is TRUE, the adaptation rate associated with the triggering conditions and events of logical block 163-2 is selected at logical block 166-2 and provided to the coefficient calculator 20. If the value of logical block 163-2 is FALSE, then it is determined if the next highest priority triggering conditions exist or events have occurred. The process proceeds until, at logical block 163-*n*, it is determined if the lowest (or nth highest) priority triggering conditions exist or events have occurred. If the value of logical block 163-*n* is TRUE, the adaptation rate associated with the lowest priority triggering conditions or events is selected at logical block **166-*n* and provided to the coefficient calculator 20. If the value of logical block 163-*n* is FALSE, at logical block 167 the default adaptation rate is selected and provided to the coefficient calculator 20**.

In one implementation of FIG. 5A, there are two alternate adaptation rates (n=2). One triggering event is that the frequency of the reference input signal is at or near a frequency at which system components are unstable, have high variance, or are operating nonlinearly, the value of μ might be relatively low, for example 0.2 so that the adaptive filter is less likely to go unstable.

If, the reference signal frequency is a frequency at which system components (such as input transducers 24, cabin filter 22, and acoustic driver 28) are stable, have little variance and are operating linearly, and if the vehicle is not undergoing rapid acceleration, the value of μ might be a relatively low default value, for example 0.1 to improve cancellation by reducing jitter in the adaptive filter.

In the implementation of FIG. 5A, The value of μ may be selected from a number of values, for example selected from a table.

In another example, the value of p is related to the rate of change of the reference frequency. During periods of rapid acceleration, it may be desirable to have a relatively high adaptation rate, to adapt more rapidly; or it may be desirable to have a relatively low adaptation rate, to avoid instabilities.

Figure 5B:
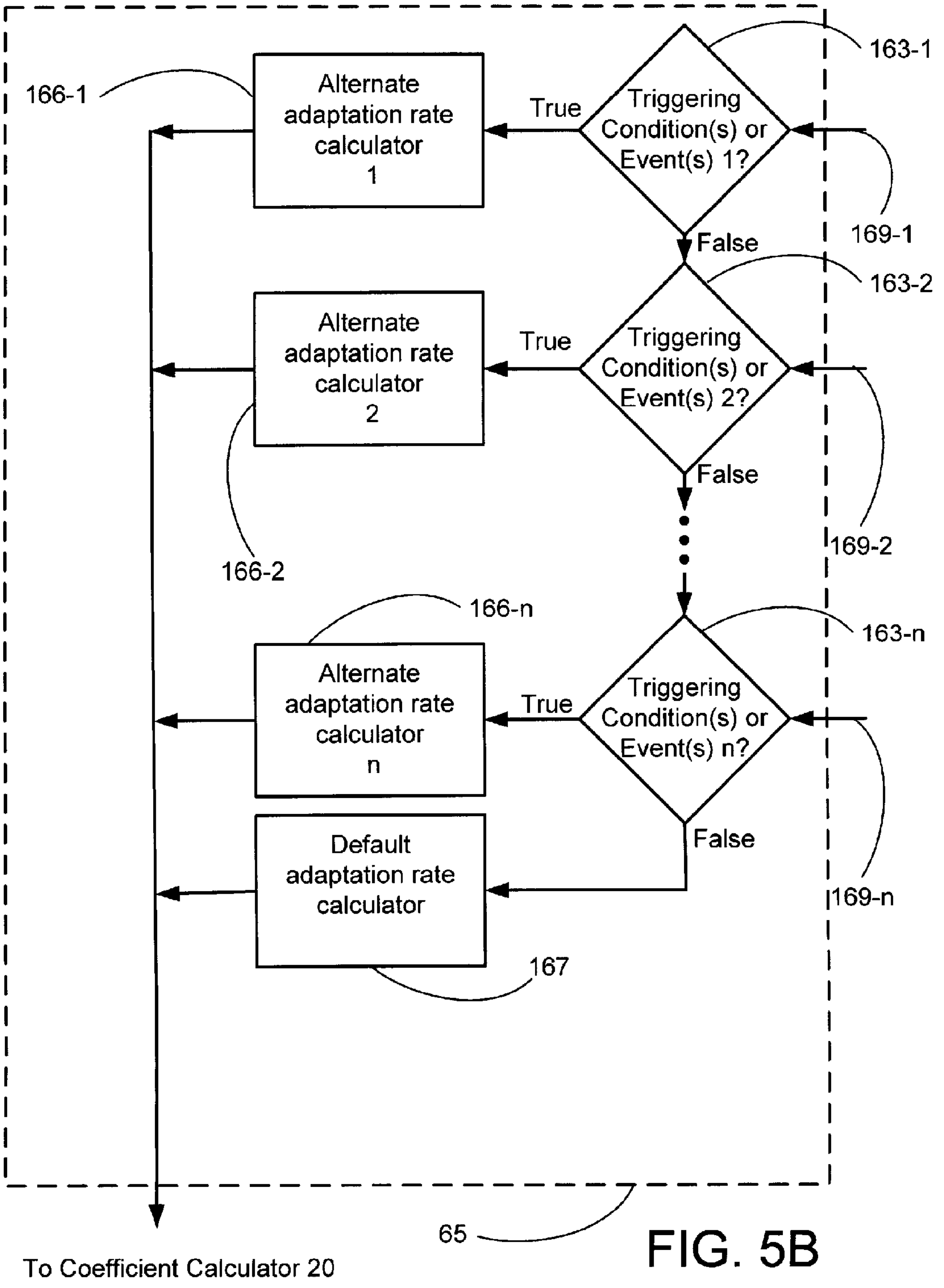

FIG. 5B shows another implementation of the adaptation rate determiner of FIG. 5A. In the adaptation rate determiner of FIG. 5B, the alternate adaptation rates at blocks **166-1-166-*n* of FIG. 5A are replaced by adaptation rate calculators 166-1 through 166-*n* and the default adaptation rate block 167 of FIG. 5A is replaced by a default adaptation rate calculator 167**. The adaptation rate calculators permit the default adaptation rate and/or the alternate adaptation rates to have a range of values instead of a single value and further permit the adaptation rate to be dependent on the triggering condition or on some other factor. The specific adaptation rate may be calculated based on a defined mathematical relationship with an element of the triggering condition, with a filter coefficient, with the cancellation signal magnitude, or with some other condition or measurement. For example, if the triggering condition is a high rate of change of the frequency of in input reference signal, the adaptation rate could be an assigned value. If the triggering condition is FALSE, the default adaptation rate could be $$\mu_{default} = \mu_{base} + \lambda\frac{df}{dt},$$

where $\mu_{base}$ is a base adaptation rate, $$\frac{df}{dt}$$

is the rate of change of the frequency of the reference input signal, and λ is a number representing the slope (which may be negative) of a linear relationship between the adaptation rate and the rate of change of the reference input signal frequency. In other examples, the adaptation rate may be determined according to a nonlinear function, for example a quadratic or exponential function, or in other examples, the slope may be zero.

Elements of the implementations of FIGS. 5A and 5B may be combined. For example, some of the alternate adaptation rates may be predetermined and some may be calculated; some or all of the alternate adaptation rates may be predetermined and the default adaptation rate may be calculated; some or all of the alternate adaptation rates may be predetermined and the default adaptation rate may be calculated; and so forth.

Referring again to FIG. 4A, the control block 37 of the active noise reduction system may include an error signal level monitor 70 and an instability control block 71. A high error signal often indicates that the system is becoming unstable, so if a high error signal is detected, the error signal monitor may adjust other system components, for example changing the adaptation rate or leakage factor, or deactivating the system. However, during rapid acceleration of the vehicle, a high error signal may indicate normal operation of the system.

An example of the operation of the error signal level monitor and the instability control block 71 is shown in FIG. 4B. At block 73, it is determined if the error signal level exceeds a predetermined level that indicates that the system may be unstable. If the error signal is not above the predetermined level, the system operates normally. If the error signal is above the predetermined level, at block 75 it is determined if the rate of change of the reference signal frequency is greater than a threshold level. If the rate of change of the reference signal frequency is above the threshold level, the system operates normally. If the rate of change of the frequency is not above the threshold level, the instability control block 71 may perform operations to correct the instability, by changing the leakage factor, changing the adaptation rate, or deactivating the system. So that the error signal level monitor can determine if the rate of change of the reference signal frequency is above the threshold level, the rate of change block 80 and the error signal level monitor 70 may be operationally coupled, as indicated in FIG. 4A.

The active noise reduction system may control the magnitude of the noise reduction audio signal, to avoid overdriving the acoustic driver or for other reasons. One of those other reasons may be to limit the noise present in the enclosed space to a predetermined non-zero target value, or in other words to permit a predetermined amount of noise in the enclosed space. In some instances it may be desired to cause the noise in the enclosed space to have a specific spectral profile to provide a distinctive sound or to achieve some effect.

Figure 6:
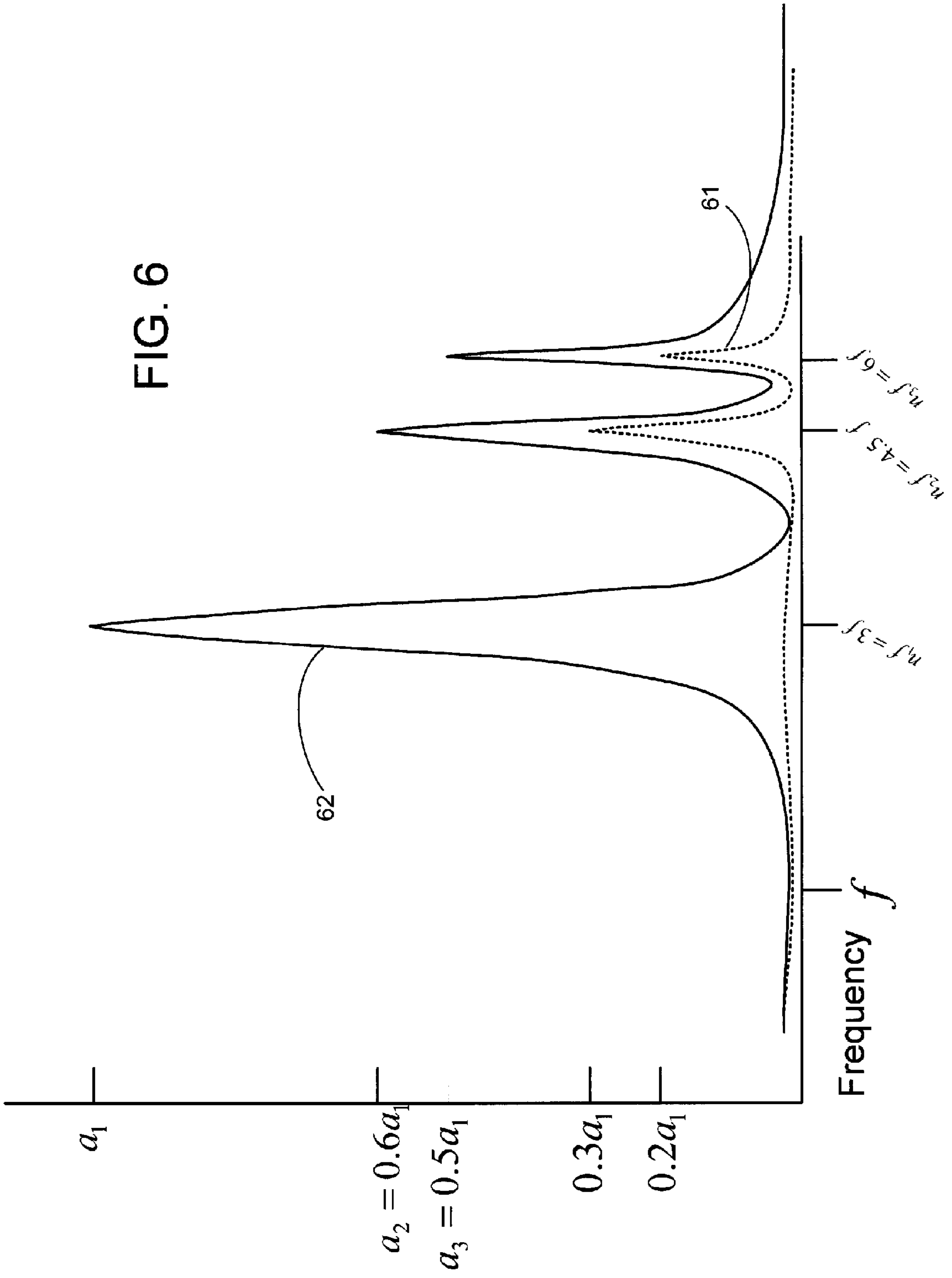
FIG. 6 is a frequency response curve illustrating an example of a specific spectral profile.

FIG. 6 illustrates an example of a specific spectral profile. For simplicity, the effect of the room and characteristics of the acoustic driver 28 will be omitted from the explanation. The effect of the room is modeled by the filter 22 of FIG. 1A or the cabin filter 22' of FIG. 1B. An equalizer compensates for the acoustic characteristics of the acoustic driver. Additionally, to facilitate describing the profile in terms of ratios, the vertical scale of FIG. 6 is linear, for example volts of the noise signal from microphone 24". The linear scale can be converted to a non-linear scale, such as dB, by standard mathematical techniques.

In FIG. 6, the frequency f may be related to the engine speed, for example $$f(\text{Hz}) = \frac{\text{engine\_speed(rpm)}}{60}.$$

Curve 62 represents the noise signal without the active noise cancellation elements operating. Curve 61 represents the noise signal with the active noise cancellation elements operating. Numbers $n_1$, $n_2$, and $n_3$ may be fixed numbers so that $n_1f$, $n_2f$ and $n_3f$ are fixed multiples of f Factors $n_1$, $n_2$, and $n_3$ may be integers so that frequencies $n_1f$, $n_2f$, and $n_3f$ can conventionally be described as "harmonics", but do not have to be integers. The amplitudes $a_1$, $a_2$, and $a_3$ at frequencies $n_1f$, $n_2f$ and $n_3f$ may have a desired characteristic relationship, for example $$a_2 = 0.6a_1$$

or $$\frac{a_2}{a_1} = 0.6$$

and $$a_3 = 0.5a_1$$

or $$\frac{a_3}{a_1} = 0.5.$$

These relationships may vary as a function of frequency.

There may be little acoustic energy at frequency f. It is typical for the dominant noise to be related to the cylinder firings, which for a four cycle, six cylinder engine occurs three times each engine rotation, so the dominant noise may be at the third harmonic of the engine speed, so in this example $n_1$=3. It may be desired to reduce the amplitude at frequency 3f ($n_1$=3) as much as possible because noise at frequency 3f is objectionable. To achieve some acoustic effect, it may be desired to reduce the amplitude at frequency 4.5f (so in this example $n_2$=4.5) but not as far as possible, for example to amplitude 0.5 $a_2$. Similarly, it may be desired to reduce the amplitude at frequency 6f (so in this example $n_3$=6) to, for example $0.4a_3$. In this example, referring to FIG. 1B, noise reduction reference signal generator 19 receives the engine speed from the engine speed signal delivery system and generates a noise reduction reference signal at frequency 3f The coefficient calculator 16 determines filter coefficients appropriate to provide a noise reduction audio signal to drive the amplitude at frequency 3f toward zero, thereby determining amplitude $a_1$. In instances in which the noise at frequency 3f is not objectionable, but rather is desired to achieve the acoustic effect, the adaptive filter may null the signal at frequency 3f numerically and internal to the noise reduction system. This permits the determination of amplitude $a_1$ without affecting the noise at frequency 3f Noise reduction reference signal generator 19 also generates a noise reduction signal of frequency 4.5f and coefficient calculator 20 determines filter coefficients appropriate to provide a noise reduction signal to drive the amplitude $a_2$ toward zero. However, in this example, it was desired that the amplitude at frequency 4.5f to be reduced to no less than 0.5 $a_2$. Since it is known that $a_2$=$0.6a_1$, the alternate leakage factor is applied by the leakage adjuster 18 when the noise at frequency 4.5f approaches $(0.5)(0.6)a_1$ or $0.3a_1$. Similarly, the alternate leakage factor is applied by leakage adjuster 18 when the noise at frequency 6f approaches $(0.4)(0.5)a_1$ or $0.2a_1$. Thus, the active noise reduction system can achieve the desired spectral profile in terms of amplitude $a_1$.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. A method for operating an active noise reduction system comprising:
- providing filter coefficients for an adaptive filter in response to a noise signal;
- determining leakage factors;
- smoothing the leakage factors to provide smoothed leakage factors;
- applying the smoothed leakage factors to the filter coefficients to provide modified filter coefficients; and
- applying the filter coefficients to an audio signal;
- wherein the determining comprises determining a leakage factor as a function of the frequency of an input reference signal.

2. A method in accordance with claim 1, wherein the applying comprises multiplying an old filter coefficient value and a filter coefficient update amount by the smoothed leakage factors.

3. An active noise reduction system comprising:
- an adaptive filter, for providing an active noise reduction signal;
- a coefficient calculator, for providing filter coefficients for the adaptive filter;
- a leakage adjuster comprising a data smoother to provide smoothed leakage factors to apply to the filter coefficients, and further comprising circuitry to determine leakage factors as a function of the frequency of an input reference signal and to provide the leakage factors to the data smoother; and
- circuitry for applying the coefficients to an audio signal.

4. A method for operating an active noise reduction system comprising:
- providing filter coefficients of an adaptive filter in response to a noise signal;
- determining leakage factors associated with the filter coefficients, wherein the determining comprises
- in response to a first triggering condition, providing a first leakage factor;
- in response to a second triggering condition, providing a second leakage factor, different from the first leakage factor; and
- in the absence of the first triggering condition and the second triggering condition, providing a default leakage factor; and
- applying the filter coefficients to an audio signal;
- wherein at least one of the providing the first leakage factor, providing the second leakage factor, and providing the default leakage factor comprises determining the leakage factor value as a function of the frequency of a reference input signal.

5. A method comprising:
- determining a leakage factor for use in an adaptive filter of a noise reduction system as a function of the frequency of an input reference signal;
- applying the leakage factor to coefficients of the adaptive filter; and
- applying the coefficients to an audio signal.

6. A method in accordance with claim 5, further comprising applying the leakage factor to a filter coefficient update amount.

7. A method in accordance with claim 5, wherein the method is incorporated in the operation of an active noise reduction system.

8. A method in accordance with claim 7, wherein the method is incorporated in the operation of an active noise reduction system in a vehicle.

9. A method in accordance with claim 5, wherein the applying the leakage factor comprises combining the adaptive filter coefficient value and the coefficient value update amount prior to the applying the leakage factor.

10. A method in accordance with claim 5, wherein the applying the leakage factor comprises:

applying the leakage factor to the adaptive filter coefficient value to provide a modified adaptive filter coefficient value;

applying the leakage factor to the coefficient value update amount to provide a modified coefficient value update amount; and combining the modified adaptive filter coefficient value and the modified coefficient value update.

* * * * *